(12) United States Patent
Liu

(10) Patent No.: US 9,211,317 B2
(45) Date of Patent: Dec. 15, 2015

(54) METHOD OF USING PROUROKINASE IN FACILITATED PERCUTANEOUS CORONARY INTERVENTION IN PATIENTS WITH ACUTE MYOCARDIAL INFARCTION

(76) Inventor: Jianning Liu, Jiangsu (CN)

( * ) Notice: Subject to any disclaimer, the term of this patent is extended or adjusted under 35 U.S.C. 154(b) by 370 days.

(21) Appl. No.: 12/935,161

(22) PCT Filed: Apr. 1, 2008

(86) PCT No.: PCT/CN2008/070653
§ 371 (c)(1), (2), (4) Date: Sep. 28, 2010

(87) PCT Pub. No.: WO2009/121223
PCT Pub. Date: Oct. 8, 2009

(65) Prior Publication Data
US 2011/0229454 A1 Sep. 22, 2011

(30) Foreign Application Priority Data
Mar. 31, 2008 (CN) .......................... 2008 1 0020100

(51) Int. Cl.
*A61K 38/49* (2006.01)
*C12N 9/64* (2006.01)

(52) U.S. Cl.
CPC .............. *A61K 38/49* (2013.01); *C12N 9/6424* (2013.01)

(58) Field of Classification Search
CPC ............ A61K 2300/00; A61K 31/198; A61K 9/0019; A61K 31/60; A61K 45/06; A61K 31/616; A61K 38/1833; A61K 38/30; A61K 31/22; A61K 31/519; A61K 38/18; A61K 31/44; A61K 31/5377; A61K 38/06; A61K 48/00; A61K 31/40; A61K 31/47
See application file for complete search history.

(56) References Cited

U.S. PATENT DOCUMENTS

| | | | | |
|---|---|---|---|---|
| 5,030,448 A | * | 7/1991 | Hunter | 424/78.38 |
| 5,041,288 A | * | 8/1991 | Hunter | 424/78.38 |
| 5,047,236 A | * | 9/1991 | Hunter | 424/78.38 |
| 5,050,064 A | * | 9/1991 | Mayhew | 700/67 |
| 5,051,264 A | * | 9/1991 | Ambrus | 424/94.2 |
| 5,626,841 A | * | 5/1997 | Gurewich | 424/94.63 |
| 5,674,192 A | * | 10/1997 | Sahatjian et al. | 604/28 |

OTHER PUBLICATIONS

Brodie Heart 2005: 91:1527-1529.*
International Search Report of PCT/CN2008/070653.

\* cited by examiner

*Primary Examiner* — Blaine Lankford
(74) *Attorney, Agent, or Firm* — Global IP Services; Tianhua Gu

(57) ABSTRACT

In the field of biological medicines, a use of prourokinase (proUK) and variants thereof in facilitated percutaneous coronary intervention (PCI) in patients with acute myocardial infarction is provided. The use includes: within 6 hrs after a patient is afflicted with accurate myocardial infarction (AMI), firstly, performing thrombolytic therapy with proUK or variants thereof, and then, performing a PCI operation, to dredge the infarction related artery (IRA) as soon as possible, and re-establish an effective forward blood flow, such that an ischemic myocardium is reperfused. According to the present invention, the facilitated PCI for treatment of AMI with the proUK or variants thereof has an effect superior to that of direct PCI.

6 Claims, 1 Drawing Sheet

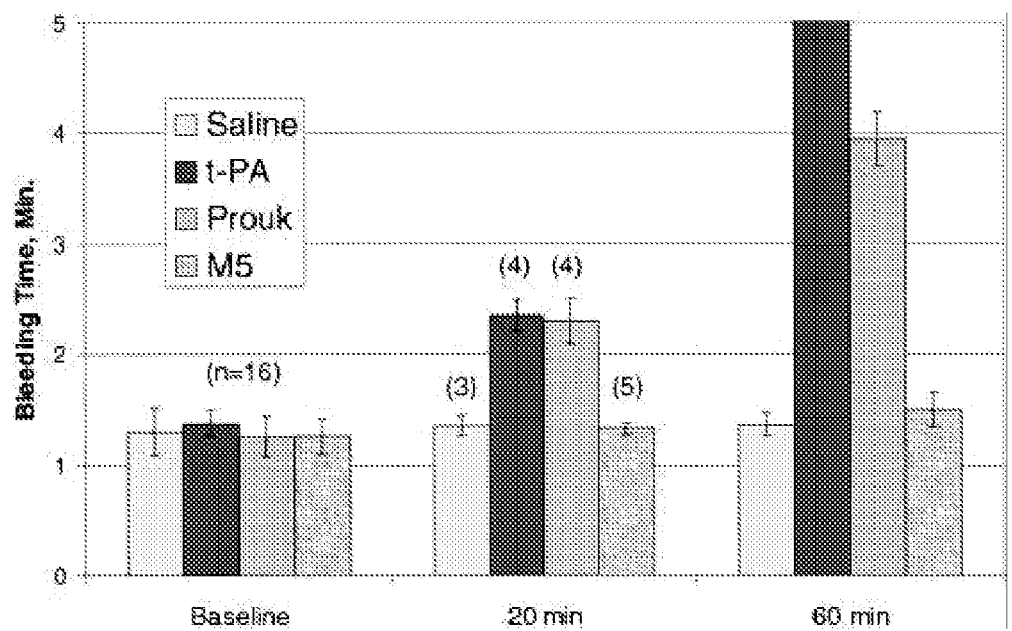

METHOD OF USING PROUROKINASE IN FACILITATED PERCUTANEOUS CORONARY INTERVENTION IN PATIENTS WITH ACUTE MYOCARDIAL INFARCTION

CROSS REFERENCE TO RELATED PATENT APPLICATION

The present application is the US national stage of PCT/CN2008/070653 filed on Apr. 1, 2008, which claims the priority of the Chinese patent application No. 200810020100.5 filed on Mar. 31, 2008, which application is incorporated herein by reference.

BACKGROUND OF THE INVENTION

1. Field of Invention

The present invention relates to the field of biological medicines, and more particularly to a use of a plasminogen activator prourokinase (proUK) and variants thereof in facilitated percutaneous coronary intervention (PCI) in patients with accurate myocardial infarction (AMI).

2. Related Art

It is a most important strategy, in early-stage treatment of AMI, to dredge the infarction related artery (IRA) as soon as possible to re-establish an effective forward blood flow, such that an ischemic myocardium is reperfused.

Direct PCI and intravenous thrombolytic therapy are two main methods for dredging the IRA and performing reperfusion to reduce the mortality.

The optimal time for reperfusion to treat AMI is within 1 hr after the onset of the chest pain, and it is critical for reducing the mortality and the disability rate to shorten the time from the onset of the chest pain to the effective reperfusion of the ischemic myocardium. If a direct PCI is performed within 90 min after the medical visit of a patient, the therapeutic effect of the PCI is superior to that of a thrombolytic therapy[1,2,3]. However, due to the limitations such as the PCI equipment in the local medical institution where the patient visits, whether a skilled operator can be in position timely, and inevitable time delay during the transportation of a patient, even in American with very advanced medical services, only 4% of the patients after referral can achieve the treatment objective of receiving direct PCI for reperfusion within 90 min after the medical visit, and about 60-70% of the patients cannot receive direct PCI therapy in time[4].

It is found through studies that, the 30-day mortality of the group of patients that arrive at hospital within 3 hrs after the onset of the chest pain and receive thrombolytic therapy is similar to and even lower than that of the direct PCI group[5,6], and when the delay time of the direct PCI reaches 62 min, compared with the thrombolytic therapy, there is no marked difference in 4-6-week mortality between the two therapy methods[7].

Facilitated PCI refers to an AMI therapeutic schedule in which a thrombolytic drug is administered to an AMI patient for treatment before PCI and then PCI is performed. It is suggested in the AMI treatment guideline of American Heart Association (AHA)/American College of Cardiology (ACC) that, if a direct PCI cannot be implemented within 90 min in the first-visited hospital, the thrombolytic therapy should be immediately implemented on patients without contraindications of thrombolytic therapy; as for patients within 3 hrs after onset, if the conditions for the direct PCI are not satisfied or the delay time of the direct PCI is longer than 1 hr, the thrombolytic therapy is preferred[1]. Due to the feasibility and effectiveness, the thrombolytic therapy is still a reperfusion therapy received by most of the AMI patients, which means that the facilitated PCI has important application meanings in clinical treatment of AMI. However, the effectiveness and safety of the facilitated PCI by using presently approved thrombolytic drugs, such as streptokinase and TPA (including, for example, TNK, reteplase, and alteplase) are significantly poorer than those of the direct PCI[8,9], which may be related to that the TPA thrombolytic drugs may activate the coagulation system upon use and thus the incidence rate of reinfarction is high. Therefore, there is an urgent need to find a new thrombolytic drug applicable in the facilitated PCI.

proUK (which contains 411 amino acids, and has a molecular weight of 46393.65 dalton and an amino acid sequence as shown in SEQ ID NO.1) is a serine proteolysis zymogen having dual characteristics of enzyme and zymogen. After entering the blood circulation intravenously, as a zymogen, proUK or variants thereof will not cause systematic plasminogen activation; and as an enzyme, proUK or variants thereof can dissolve the embolized thrombus with a high selectivity, without acting on hemostatic thrombus at wounds at tissues and organics, and thus prevent hemorrhagic complications upon thrombolytic therapy to the utmost extent. As proUK or variants thereof also have the function of inhibiting platelet aggregation, the incidence rate of reinfarction after thrombolysis may be reduced. It is shown by study results that when treating AMI with rh-PROUK thrombolytic therapy, at 90 min after the administration, the dredging rate of IRA is equivalent to that of TPA, after 24 hr, the reinfarction rate is lower than that of TPA and streptokinase, and after 30 days, the mortality of the patient is lower than that of TPA, streptokinase, and urokinase[10,11]. Presently, there is no report about use of proUK or variants thereof in facilitated PCI in patients with AMI in documents.

SUMMARY OF THE INVENTION

The present invention is directed to a use of proUK and variants thereof in facilitated PCI in patients with AMI.

The objectives of the present invention are realized through the following technical solutions.

The present invention provides a use of proUK and variants thereof in facilitated PCI in patients with AMI.

The use includes: within 6 hrs after a patient is afflicted with AMI, firstly, performing thrombolytic therapy with proUK or variants thereof, and then, performing a PCI operation, to dredge the infarction related artery (IRA) as soon as possible, and re-establish an effective forward blood flow, such that an ischemic myocardium is reperfused.

In the use, proUK is a natural proUK or a recombinant human proUK, and has an amino acid sequence as shown in SEQ ID NO.1.

In the use, the variants of proUK are proteins or polypeptides with one or more amino acids replaced, deleted, or added in the amino acid sequence of proUK and having proUK activity; proteins with higher than 40% homology with the whole sequence of the natural proUK protein; or proteins or polypeptides with higher than 90% homology with the B chain sequence of the natural proUK protein.

In the use, the variants of proUK are proUKs having a lysine (Lys) at position 300 in the amino acid sequence of proUK as shown in SEQ ID NO.1 site-mutated into histidine (His).

In the use, the thrombolytic therapy with proUK or variants thereof is performed in a manner of intravenous bolus at a dose of 500,000 units-3,000,000 units per patient; in a manner of intravenous drip infusion for 30-120 min at 50,000 units-200,000 units/min/patient; or in a manner of intravenous bolus and intravenous drip infusion in combination, including first administrating in the manner of intravenous bolus of 20% of the total dose of proUK to each patient, and then in the manner of intravenous drip infusion for 90 min at 50,000 units-200,000 units/min for the rest, in which the total dose of proUK or variants thereof is not greater than 6,000,000 units.

In the use, an administration time of the thrombolytic therapy with proUK or variants thereof is 5 min-120 min.

In the use, the PCI operation is performed at half an hour to 24 hrs after the thrombolytic therapy with proUK or variants thereof.

In the use, the PCI operation is performed at 1 day to 7 days after the thrombolytic therapy with proUK or variants thereof.

The present invention has the following beneficial effects.

According to the present invention, in the study of phase II clinical trial of the recombinant human proUK (Drug Clinical Trial Approval No. 2003L03626, issued by State Food and Drug Administration), it is found that among 38 patients in an angiography group, 28 patients receive PCI immediately after thrombolysis with recombinant human proUK, in which one patient receives PTCA, and the other 27 patients have a stent implanted after PTCA (that is, receive a PCI), as a result, the 30-day mortality and 6-month mortality are both zero, the incidence rates of reinfarction, stroke, moderate hemorrhage and severe hemorrhage are all zero, and no "no-reflow" phenomenon occurs.

Clinical observation results show that, the facilitated PCI for treatment of AMI performed immediately after thrombolysis with the recombinant human proUK has a clinical therapeutic efficacy superior to that of the direct PCI.

The reason for the good effect of the combination of proUK or variants thereof and PCI lies in that, proUK or variants thereof are serine proteolysis zymogens having dual characteristics of enzyme and zymogen. After entering the blood circulation intravenously, as a zymogen, proUK or variants thereof will not cause systematic plasminogen activation; and as an enzyme, proUK or variants thereof can dissolve the embolized thrombus with a high selectivity, without acting on hemostatic thrombus at wounds at tissues and organics, and thus prevent hemorrhagic complications upon thrombolytic therapy to the utmost extent. As proUK or variants thereof also have the function of inhibiting platelet aggregation, the incidence rate of reinfarction after thrombolysis may be reduced. The reinfarction rate of AMI treated with proUK or variants thereof is much lower than that of tPA, such that the opportunity of reinfarction after implanting the stent during the PCI operation is reduced, and thus the mortality is significantly reduced.

BRIEF DESCRIPTION OF THE DRAWINGS

The present invention will become more fully understood from the detailed description given herein below for illustration only, and thus are not limitative of the present invention, and wherein:

FIG. 1 shows a bleeding staunching test result in dogs according to a second embodiment, in which at the initial bleeding time (mean±SD), dogs (the number of the dogs in each group is as shown by the numeral in the brackets in the FIGURE) are infused with saline, tPA, proUK, and MS (60 µg/kg/min) respectively.

DETAILED DESCRIPTION OF THE INVENTION

Hereinafter, the present invention is further described with reference to embodiments.

Embodiment 1: ProUK and Variants Thereof

ProUK was an extracted natural proUK or a recombinant human proUK, and had an amino acid sequence as shown in SEQ ID NO.1.

The variants of proUK were proteins or polypeptides with one or more amino acids replaced, deleted, or added in the amino acid sequence of proUK and having proUK activity; proteins with higher than 40% homology with the whole sequence of the natural proUK protein; or proteins or polypeptides with higher than 90% homology with the B chain sequence of the natural proUK protein.

A specific example of the variants of proUK was proUK having a lysine (Lys) at position 300 in the amino acid sequence of proUK as shown in SEQ ID NO.1 site-mutated into histidine (His).

ProUK and variants thereof can be prepared by a gene engineering method well-known in the art.

Embodiment 2: In-vivo and In-vitro Experiments Indicate that a Specific Example of the Variants of proUK (Having a Lysine (Lys) at Position 300 in the Amino Acid Sequence of proUK as Shown in SEQ Id NO.1 Site-Mutated into Histidine (His), Lys300 →His, M5) has a Thrombolytic Activity at Least Equivalent to or Superior to that of proUK, and Thus is Applicable in Facilitated PCI Therapy (1) In-vitro Experimental Results of M5

1.1 Intrinsic Catalytic Activity Test

As for the hydrolysis of a chromophoric substrate S2444 (L-pGlu-L-Gly-Arg p-nitroanilide hydrochloride), 1.0 mol/L proUK or 100 mol/L M5 and a series of concentrations (0-2.4 mmol/L) of S2444 were co-incubated in a buffer solution (0.05 mol/L Tris-HC1, 0.10 mol/L NaC1, and 0.01% Tween 80, pH 7.4) at room temperature, the reaction rate was determined by an increment in light absorption at 410 nm, and the reaction constant was calculated through a Lineweaver-Burk plot. The results show that, the lag phase of MS is twice that of the proUK, but the rate is rapidly increased subsequently, which respectively indicate that M5 has a relatively low intrinsic activity and a relatively high dual-strand catalytic activity.

1.2 Promotion of Co-Factor on Plasminogen Activation Caused by proUK or M5

The effect of fibrin fragment E on the plasminogen activation caused by proUK or MS was studied by plasmin tolerant proUK and M5 variant (Lys158). At room temperature, the increment in light absorption with time at 410 nm of the reaction mixture (containing 15 mmol/L S2251 (D-Val-L-Leu-L-Lys p-nitroanilide dihydrochloride), 20 mol/L Glu-fibrinogen, and 1.0 nmol/L Ala158-proUK or Ala158-M5, and containing 5.0 mol/L fragment E2 or not) was determined. The effect of the fibrin analogs, such as fibrinogen, soluble fibrin monomer, and D-dimer, on the plasminogen activation was also studied, because they could not promote the urokinase-mediated plasminogen activation. The experimental results show that, the fibrin fragment E is capable of selectively promoting the plasminogen-activating function of proUK, and has the similar effect on M5, while D-dimer and the soluble fibrin or fibrinogen almost have no promotion effect on the plasminogen activation caused by proUK or MS.

1.3 Inhibition Effect of PAI-1

The dual-strand tc-M5 was inhibited by PAI-1, in which the value of K was about $1.3\pm0.3\times10^7$ mol/L·s, and was equivalent to that ($1.7\pm0.4\times10^7$ mol/L·s) of urokinase.

1.4 Stability (Inactivity) of M5 and ProUK in Human Plasma 0-20 μg/mL M5 or 0-8 μg/mL proUK was incubated in 1 mL mixed plasma containing an anticoagulant citrate at 37° C. for 6 hrs, 0.2 mL aprotinin (10000 kallikrein inhibition units per mL). The amount of the fibrinogen remained in the plasma was determined by a thrombin coagulable protein method, and compared with a baseline.

In the mixed plasma, M5 maintained inactive, and did not cause the degradation of the fibrinogen at a dose lower than 8 μg/mL, and at a dose of 10 μg/mL, there was still 30.6% fibrinogen maintained to be undegraded. On the contrary, proUK caused the degradation of the fibrinogen at a dose of 2 μg/mL, and at a dose of 4 μg/mL, only 32.7% fibrinogen was maintained to be undegraded.

1.5 In-vitro Dissolving Effect of ProUK and M5 in Human Plasma on Blood Clots $I^{125}$ labelled fibrinogen clot was made from 0.2 mL plasma, and was incubated in 4 mL plasma. A series of concentrations of fibrin specific proUK (0.5-1.5 μg/mL) or M5 (0.5-5.0 μg/mL) were tested, in which the dissolution of the blood clot was expressed by a ratio percentage of a complete dissolution value to time, and the fibrinogen was determined after the blood clot was completely dissolved; and if the blood clot was not completely dissolved after 6 hrs, the fibrinogen was determined at 6 hrs.

In the plasma environment, the M5 still maintained the fibrin specificity at a concentration as high as 5 μg/mL (in which 25% fibrinogen was degraded), and as for proUK, the upper limit was 1.5 μg/mL. The maximal blood clot dissolving rate of proUK was 41% per hour, while the maximal blood clot dissolving rate of M5 was 64% per hour. When M5 (2 μg/mL) was used in combination with a small amount of tPA (30 ng/mL), the lag phase was halved, which was similar to the result of the combination of tPA and proUK.

(2) In-vivo Study of M5

2.1 Dissolution of Dog Blood Clot 10-15 kg male mongrels were anaesthetized with pentobarbital sodium. The blood clot was made from 1 mL dog whole blood added with $I^{125}$ labeled fibrinogen (1.9 Ci, 0.75 mCi/mg protein) and thrombin (10 units). After 20 min, the blood clot was washed three times with saline, cut into small pieces of 1 mm, and then injected into the femoral vein with a 16 gauge needle. After 15 min, a blood sample was taken through a catheter out of the femoral vein on the other side and determined for baseline radioactivity. Next, saline, proUK, or tPA was intravenously administered respectively, and the infusion rates of proUK and tPA were 20 μg/kg/min and 10 μg/kg/min respectively, which were effective for thrombolysis in the dog body and had fibrin specificity according to the report in previous documents. The infusion of tPA was maintained for 60 min, and the infusion of proUK and M5 were maintained for 90 min. The infusion rates of M5 were 20 g/kg/min, 40 g/kg/min, and 60 g/kg/min respectively, and after a certain interval, blood samples were taken and determined for radioactivity and fibrinogen.

The experimental results show that, the blood clot dissolution caused by M5 is dose-dependent. As the stability of M5 in the plasma is four times higher than that of the proUK, and when being infused at a rate of 60 μg/kg/min, M5 causes rapid blood clot dissolution, and the blood clot dissolution is up to 100% within 45 min. The blood clot dissolution caused by M5 is more effective, because only 600 μg/kg M5 is needed for achieving 50% dissolution, and the dose is 1200 μg/kg for proUK. At a lower dose (40 μg/kg/min or 20 μg/kg/min), the blood clot dissolution caused by M5 is equivalent to or less than that of proUK. The relatively low effectiveness at a low dose reflects a longer lag phase of M5. The concentrations of the plasma fibrinogen of the test dogs in the group with the maximal infusion dose of M5 are 72%, 65%, and 52% of the baseline level at 30 min, 45 min, and 60 min.

2.2 Dog Bleeding Staunching Test

A 1 cm standard incision was made at the shaved abdomen, and the epidermis was stripped. An exposed superficial vein was sliced with a surgical scapel, and a bleeding point was patted once with a filter paper every thirty seconds, till the bleeding stopped. This time was recorded as initial bleeding time (BT), which was determined at the adjacent 1 cm incision sites at 0 min, 20 min, and 60 min. The total amount of bleeding was recorded as the number of the standard gauze swabs (5×5 cm) needed for absorbing blood oozed from the wound, and each gauze swab was replaced after absorbing enough blood. This represented secondary bleeding, because the blood was mainly from the two previous bleeding points staunched after determining the initial BT. The experiment was performed at 60 min before each infusion.

The experimental results (as shown in FIG. 1) show that, in a tPA infusion group, the initial BT is increased from 1.2 min to 2.4 min at 20 min after infusion, and is increased to 5 min at 60 min after infusion, and in a proUK group, the initial BT is increased to 4 min. As for an M5 dose group, the BT is not prolonged significantly at 20 min, and at 60 min, the BT is increased to be 1.5 min. This indicates that the total bleeding quantity represented by the number of the gauze swabs needed for absorbing blood during the secondary bleeding is increased by 8 times in the tPA group, and is increased by 5 times in the proUK group, and is not increased in the group with the maximal dose of MS.

2.3 Dissolution of Rhesus Monkey Blood Clot and Bleeding Staunching Test

The sensitivity of rhesus monkey to human proUK/urokinase is similar to that of human being. Six rhesus monkeys (three females, and three males) of 5.8 kg to 8.6 kg were anaesthetized by intravenously administering pentobarbital sodium (30 mg/kg), and polyethylene catheters were inserted into the veins of the upper limbs at each side for sampling blood and infusion respectively. 2 mL whole blood sample was mixed with radioactive iodine labeled fibrinogen and thrombin, and then incubated at 37° C. for 20 min. The whole blood clot was cut into 1 mm small pieces, and was washed six times with saline. The blood clot (3.3-10 cpm) was suspended in 5 mL saline, and infused through the vein of the right upper limb. After 30 min, a blood sample was taken from the vein of the upper limb at the opposite side, and determined for the baseline radioactivity. Meanwhile, saline (2 monkeys) or M5 (4 monkeys) was infused. M5 was infused at 60 μg/kg/min for 60 min, and the blood was sampled at a certain interval during the infusion for determining the radioactivity and fibrinogen. At 0 min, 30 min, 45 min, and 60 min, the initial BT was determined at an incision of 5 mm long and 1 mm deep at the lower abdomen. The BT was determined by a standard method by patting once with a filter paper every thirty seconds. The re-BT of the initial bleeding point after staunching was also evaluated.

The experimental results show that, 60 min infusion of M5 at 60 μg/kg/min causes 100% blood clot dissolution in all the four monkeys (only 8% in the control group). The concentrations of fibrinogen at 30 min, 45 min, and 60 min after infusion are respectively 78%, 66%, and 57% of the baseline level. The initial BT (expressed in percentage of the baseline level) is reduced to 85% at 30 min, returns to the baseline level at 45 min, and is significantly increased to 108% at 60 min. BT has similar results in the saline control group. Further-more, consistent to the results in the dogs, no rebreeding occurs in the test monkeys administered with M5.

Embodiment 3 Application of ProUK in Facilitated PCI (1) Selection Criteria
1.1 Ischemic chest pain lasting for 30 min or more, and sublingual administration of nitroglycerin being ineffective;
1.2 Sustained ischemic chest pain lasting for 12 hrs or less;
1.3 Electrocardiogram (ECG) having at least two or more ST segment elevations of 0.1 mV or more in limb lead, or two or more adjacent ST segment elevations of 0.2 mV or more in chest lead; and
1.4 Age of 85 years old or less, male or female.
(2) Exclusion Criterion
2.1 Non-ST segment-elevation AMI or unstable angina pectoris;
2.2 Women during pregnant stage, breast-feed stage, and menstrual period;
2.3 Hemorrhagic stroke occurred at anytime in the past, and ischemic stroke or cerebrovascular event occurred in 1 year;
2.4 Severe progressive diseases (such as malignant tumor) or diseases with poor prognosis and making the patient to be extremely exhausted;
2.5 Active visceral hemorrhage (such as hemorrhage of gastrointestinal tract, and hemorrhage of genito-urinary system, except for menstruation) occurred in four weeks, or uncured peptic ulcer existing;
2.6 Intracranial tumor, suspicious aortic dissection, arteriovenous malformation, and aneurysm;
2.7 After an active antihypertensive therapy, patients with hypertension still having a blood pressure equal to or higher than 170/110 mmHg, (systolic pressure or diastolic pressure meeting this blood pressure criterion);
2.8 Current use of therapeutic dose of anticoagulant drug, such as Warfarin;
2.9 Known hemorrhagic tendency (hemostasis or coagulation dysfunction);
2.10 History of new (in 6 months) brain or spinal surgery;
2.11 Hhistory of injury in two months, including traumatic cardiopulmonary resuscitation or long-time (longer than 10 min) cardiopulmonary resuscitation, or major surgery; or history of head injury in 6 months;
2.12 Macrovascular puncture at site that cannot be compressed in two weeks;
2.13 Highly suspicious thrombosis in left ventricle (such as mitral stenosis with atrial fibrillation);
2.14 History of fundus hemorrhage caused by diabetes or other diseases;
2.15 History of severe liver and renal dysfunction (ALT>three times of the normal upper limit; and creatinine>225 μmol/L);
2.16 Shock;
2.17 Infective endocarditis, acute myocarditis, acute pericarditis, septic thrombophlebitis, and arteriovenous fistula in severely infected sites;
2.18 Reinfarction at the same site;
2.19 Patients being in clinical trial of other drugs of the same class; and
2.20 Considered by a physician to have other disease and conditions not suitable for intravenous thrombolysis.
(3) Clinical Use Method (Usage, Dosage, and Administration Time)
Facilitated PCI of proUK: First, thrombolytic therapy was performed by using a recombinant human proUK through, for example, intravenous bolus, at a dose of 500,000 units-3,000,000 units per patient; intravenous drip infusion, at 50,000 units-200,000 units/min/patient for 30-120 min; or intravenous bolus and intravenous drip infusion in combination (first administrating in the manner of intravenous bolus of 20% of the total dose of proUK to each patient, and then in the manner of intravenous drip infusion for 90 min at 50,000 units-200,000 units/min for the rest), in which the total dose of proUK or variants thereof was not greater than 6,000,000 units. In the hrombolytic therapy with proUK, an administration time was 5-90 min, and then a PCI operation for treatment was performed at half an hour to 24 hrs after the thrombolytic therapy with proUK. Under specific conditions, the PCI operation for treatment might be performed at 1 day to 7 days after the thrombolytic therapy with proUK.

(4) Angiocardiography
Part of the patients received angiocardiography examination, to observe the recanalization of the IRA shown by the coronary angiographies at 90 min after the intravenous injection of the thrombolytic drug and after performing the PCI operation.

4.1 Coronary Angiography
Preceding infarction-related coronary angiography (determined according to the infarction part in ECG) was performed. The initial angiography should adopt large visual field (small image), to observe all the blood vessels, and the exposure should be lasted till the contrast agent was exhausted. The left coronary artery should be projected through at least three body positions, and the right coronary artery should be projected through at least two body positions, and large image was adopted. Before IRA angiography, no nitroglycerin was administrated through the coronary artery. The angiographic results were determined according to the TIMI perfusion grading standards, and the recanalization of the blood vessel was considered to be achieved when Grades 2 and 3 were reached.

TIMI Perfusion Determination Standard
TIMI Grade 0: The infarcted coronary artery has no forward blood flow perfused;
TIMI Grade 1: The distal vessel of the coronary artery stenosis lesion has forward blood flow perfused, but the distal vascular bed cannot be filled;
TIMI Grade 2: The distal vessel of the coronary artery stenosis lesion has forward blood flow perfused, but the distal vascular bed can be substantially fully filled slowly only after three or more cardiac cycles, and the removal of the contrast agent is slow;
TIMI Grade 3: The distal vessel of the coronary artery stenosis lesion has forward blood flow perfused, and the distal vascular bed can be fully and rapidly filled with the contrast agent (after less than three cardiac cycles), and meanwhile, the removal of the contrast agent is rapidly.

4.2 Post-Angiography Treatment
After coronary angiography, if no further therapy such as PTCA and stent implantation was needed, the arterial sheath could be removed only when APTT was lower than 80, and hemostasis was performed by locally compressing for at least half an hour or more. Heparin infusion was stopped at 48 hrs after thrombolysis, and then hypodermic injection of the low-molecular-weight heparin was performed once per 12 hrs for 5 days.

(5) Clinical and Laboratory Observation Indexes
5.1 Clinical Symptoms and Physical Signs
5.1.1 Chest Pain: relief or not and relief degree
Evaluation was performed according to the following four grades: no change, mildly relief (50%), significant relief (75%), and complete relief;

5.1.2 Hemorrhage Manifestation: whether there were hemorrhage signs and symptoms in skin, mucous membranes, sputum, vomit, and stool and urine;

Three grades, mild, moderate, and severe, were divided according to the following standards.

Mild: mildly hemorrhage, no need for transfusion of blood, without causing changes in hemodynamics, and including subcutaneous hemorrhage, small hematoma, oozing of blood at pinprick site.

Moderate: moderate hemorrhage, and needing for transfusion of blood, without causing the abnormal changes in hemodynamics that need for treatment, and including large hematoma, operation (such as cardiac catheterization) caused hemorrhage, or retroperitoneal hemorrhage verified by clinical examination or ultrasonic inspection and measurement, without causing the abnormal changes in hemodynamics, but needing for transfusion of blood.

Severe: severe hemorrhage, causing changes in hemodynamics and needing for treatment and transfusion of blood, and including acute hemorrhage in gastrointestinal tract or retroperitoneal hemorrhage. Intracranial hemorrhages are all severe hemorrhage.

5.1.3 Changes in Blood Pressure, Cardiac Rate, Rhythm of the Heart, Cardiac Sounds, and Cardiac Murmur.

5.1.4 Other Complications.

5.2 Electrocardiographic Recording: 18-lead ECG was recorded before thrombolysis, 12-lead ECG (for positive posterior wall infarction and right ventricular infarction, 18-lead ECG were recorded) was re-examined every half an hour for 2 hrs after the beginning of the thrombolysis, and full set of standard ECGs were re-examined at 3 hr. Since then, ECG was re-examined every day for 7 days, and ECG was re-examined before discharging from the hospital. The position of the lead electrode should be fixed strictly.

5.3 Routine Blood Test, Routine Urine Test, and Fecal Occult Blood Test: The tests could be performed before selection, and at 2 hrs, 6 hrs, 12 hrs, 24 hrs, 48 hrs (the requirement for the reducing of the examination times was not met in the stage II test), and the $7^{th}$ day (determined before discharging from the hospital, if the hospitalization days is less than 7 days) after the beginning of thrombolysis, and the examination time of the fecal occult blood test could be adjusted according to the urinary and fecal discharge.

5.4 Myocardial Enzyme: CK and CK-MB were examined once before selection and at 8 hrs, 10 hrs, 12 hrs, 14 hrs, 16 hrs, and 18 hrs after the onset, and subsequently examined as desired according to actual conditions.

5.5 Liver Function, Renal Function, Blood Glucose, and Electrolyte: Determinations were performed before selection and at the $7^{th}$ day after the beginning of thrombolysis.

(6) Criteria for Evaluation of Therapeutic Efficacy

The dredging rate of the IRA is taken as an evaluation criterion for therapeutic efficacy and the diagnostic standards of the dredging of the IRA includes the following.

6.1. Coronary Angiography

If coronary angiography shows that the blood flow of the infarction related vessels reaches TIMI grade 2 or 3 in 90 min after the beginning of thrombolysis, the vessels are determined as being re-dredged.

6.2. Clinical Recanalization Index 6.2.1 The elevated ST segments are rapidly depressed by 50% or more within 2 hrs after infusion of thrombolytic drug;

6.2.2 The chest pain is significantly relieved within 2 hrs after infusion of thrombolytic drug, and the relief degree is equal to or higher than 75%;

6.2.3 Within 2 hrs after infusion of thrombolytic drug, accelerated idioventricular rhythm, and atria or bundle branch block are improved or disappear suddenly, or a patient with inferior wall infarction has a transitional sinus bradycardia and sinoatrial block accompanied with or without low blood pressure.

6.2.4 Serum CK-MB enzyme peak is advanced and appears within 14 hrs after the onset, or the CK enzyme peak appears within 16 hrs.

If two or more indexes in the above four, except for the combination of the second and the third indexes, are met, the vessels are considered as being re-dredged.

6.3. Diagnostic Standards of Acute Reinfarction of IRA 6.3.1 Within 48 hrs after the successful thrombolysis, chest pain attacks again, the ST segment in ECG lead corresponding to the original infarction site is elevated again, and the chest pain lasts for a time period of 30 min or more, and cannot be relieved by sublingual administration of nitroglycerin.

6.3.2 Serum CK-MB level is raised again.

If the above two items are met, IRA can be clinically diagnosed as acute reinfarction.

6.3.3 Acute coronary angiography verifies IRA to be acute reinfarcted.

(7) Follow-up Visit

Follow-up visit of each patient in the trial was carried out for obtaining the 30-day case-fatality rate and the incidence rate of the adverse events.

(8) Data Observation and Results

In the study of phase II clinical trial of recombinant human proUK (Drug Clinical Trial Approval No. 2003L03626, issued by the State Food and Drug Administration), it is found that among 38 patients in the angiography group, 28 patients receive PCI immediately after thrombolysis with recombinant human proUK, in which one patient receives PTCA, and the other 27 patients have a stent implanted after PTCA (that is, receives the PCI), as a result, the 30-day mortality and 6-month mortality are both zero, the incidence rates of reinfarction, stroke, moderate hemorrhage and severe hemorrhage are all zero, and no "no-reflow" phenomenon occurs.

REFERENCES

1. Antman E M, Anbe D T, Amstrong T W, et al. ACC/AHA guidelines for the management of patients with ST-elevation myocardial infarction-executive summary: a report of the American College of Cardiology/American Heart Association Task Force on Practice Guidelines (Writing Committee to Rivise the 1999 Guidelines for the Management of Patients With Acute Myocardial Infarction). Circulation 2004; 110: 588-636.

2. Global Use of Strategies to Open Occluded Coronary Arteries in Acute Coronary Syndromes (GUSTO IIb) Agioplasty Substudy Investigators. A clinical trial comparing primary coronary angioplasty with tissue plasminogen activator for acute myocardial infarction. N Engl J Med 1997; 336: 1621-8.

3. Keeley E C, Boura J A, Grines C L. Primary angioplasty versus intravenous thrombolytic therapy for acute myocardial infarction: a quantitative review of 23 randomised trials. Lancet 2003; 361:13-20.

4. Nallamothu B K, Bates E R, Herrin J, et al. Times to treatment in transfer patients undergoing primary percutaneous coronary inervention in the United States: National Registry of Myocardial Infarction (NRMI)-3/4 analysis. Circulation 2005; 111:761-7.

5. Steg P G, Bonnefoy E, Chabaud S, et al. Impact of time to treatment on mortality after prehospital fibrinolysis or primary angioplasty: data from the CAPTIM randomized clinical trial. Circulation 2003; 108:2851-6.

6. Widimsky P, Budesinsky T, Vorac D, et al. Long distance transport for primary angioplasty vs immediate thrombolysis in acute myocardial infarction. Final results of the randomized national multicentre trial-PRAGUE-2. Eur Heart J 2003; 24:94-104.

7. Nallamothu B K, Bates E R. Percutaneous coronary intervention versus fibrinolytic therapy in acute myocardiial infarction: is timing (almost) everything? Am J Cardiol 2003; 92:824-6.

8. Primary versus tenecteplase-facilitated percutaneous coronary intervention in patients with st-segment elevation acute myocardial infarction (ASSENT-4 PCI): randomised trial. Lancet 2006; 367: 569-78.

9. Keeley E C, Boura J A, Grines C L. Comparison of primary and faciliated percutaneous coronary interventions for S-T elevation myocardial infarction: quantitative review of randomised trials. Lancet 2006; 367: 579-88.

10. Weaver W D, Hartmann J R, Anderson J L, Reddy P S, Sobolski J C, Sasahara A A. New recombinant glycosylated prourokinase for treatment of patients with acute myocardial infarction. J Am Coll Cardiol. 1994; 24:1242-8.

11. Zarich S W, Kowalchuk G J, Weaver W D, Loscalzo J, Sassower M, Manzo K, Byrnes C, Muller J E, Gurewich V. Sequential combination thrombolytic therapy for acute myocardial infarction: results of the Pro-Urokinase and t-PA Enhancement of Thrombolysis (PATENT) Trial. J Am Coll Cardiol. 1995; 26(2):374-9.

What is claimed is:

1. Method of facilitated percutaneous coronary intervention (PCI) for treating patients with acute myocardial infarction (AMI) comprising:

within 6 hrs after a patient is afflicted with AMI, firstly, performing thrombolytic therapy with the proUK or variants thereof, whereas the variant of proUK is proUKs having a lysine (Lys) at position 300 in the amino acid sequence of the proUK as shown in SEQ ID No.1 site-mutated into histidine (His);

then, performing the PCI operation, to dredge the infarction related artery (IRA) as soon as possible, and re-establish an effective forward blood flow, such that an ischemic myocardium is reperfused.

2. The method according to claim 1, wherein the proUK is a natural proUK or a recombinant human proUK, and has an amino acid sequence as shown in SEQ ID NO.1.

3. The method according to claim 1, wherein the thrombolytic therapy with the proUK or variants thereof is performed in a manner of intravenous bolus at a dose of 500,000 units-3,000,000 units per patient; in a manner of intravenous drip infusion for 30-120 min at 50,000 units-200,000 units/min/patient; or in a manner of intravenous bolus and intravenous drip infusion in combination, comprising first administrating in the manner of intravenous bolus of 20% of the total dose of the proUK to each patient, and then in the manner of intravenous drip infusion for 90 min at 50,000 units-200,000 units/min for the rest, in which the total dose of the proUK or variants thereof is not greater than 6,000,000 units.

4. The method according to claim 1, wherein an administration time of the thrombolytic therapy with the proUK or variants thereof is 5 min-120 min.

5. The method according to claim 1, wherein the PCI operation is performed at half an hour to 24 hrs after the thrombolytic therapy with the proUK or variants thereof.

6. The method according to claim 1, wherein the PCI operation is performed at 1 day to 7 days after the thrombolytic therapy with the proUK or variants thereof.

* * * * *

SEQUENCE LISTING

```
<160> NUMBER OF SEQ ID NOS: 1

<210> SEQ ID NO 1
<211> LENGTH: 411
<212> TYPE: PRT
<213> ORGANISM: Homo sapiens

<400> SEQUENCE: 1

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
        115                 120                 125

His Asp Cys Ala Asp Gly Lys Lys Pro Ser Ser Pro Pro Glu Glu Leu
    130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Met Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
    210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270
```

```
Arg Thr Ile Gln Thr Ile Cys Leu Pro Ser Met Tyr Asn Asp Pro Gln
        275             280                 285

Phe Gly Thr Ser Cys Glu Ile Thr Gly Phe Gly Lys Glu Asn Ser Thr
    290                 295                 300

Asp Tyr Leu Tyr Pro Glu Gln Leu Lys Met Thr Val Val Lys Leu Ile
305                 310             315                     320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340             345             350

Gln Gly Asp Ser Gly Gly Pro Leu Val Cys Ser Leu Gln Gly Arg Met
        355             360             365

Thr Leu Thr Gly Ile Val Ser Trp Gly Arg Gly Cys Ala Leu Lys Asp
    370             375             380

Lys Pro Gly Val Tyr Thr Arg Val Ser His Phe Leu Pro Trp Ile Arg
385                 390             395                     400

Ser His Thr Lys Glu Glu Asn Gly Leu Ala Leu
            405             410
```